US007608189B2

(12) United States Patent
Seidel et al.

(10) Patent No.: US 7,608,189 B2
(45) Date of Patent: Oct. 27, 2009

(54) DEVICE FOR REMOVING BACTERIAL LIPOPOLYSACCHARIDES AND/OR LIPOTEICHOIC ACIDS FROM PROTEIN-CONTAINING FLUIDS AND ITS USE FOR THE TREATMENT OF SEPSIS

(75) Inventors: Dietrich Seidel, Feldafing (DE); Karl-Siegfried Boos, Gauting (DE)

(73) Assignee: B. Braun Medizintechnologie GmbH, Melsungen (DE)

( * ) Notice: Subject to any disclaimer, the term of this patent is extended or adjusted under 35 U.S.C. 154(b) by 447 days.

(21) Appl. No.: 10/860,786

(22) Filed: Jun. 3, 2004

(65) Prior Publication Data
US 2005/0009001 A1   Jan. 13, 2005

(51) Int. Cl.
*B01D 61/00* (2006.01)
*B01D 61/14* (2006.01)
*A61M 1/34* (2006.01)

(52) U.S. Cl. .............. 210/651; 210/321.79; 210/321.8; 210/321.88; 210/321.89; 210/435; 210/483; 210/488; 210/490; 210/491; 210/500.23; 210/500.36; 210/500.38; 210/500.41; 210/503; 210/506; 210/508; 210/645; 210/650; 210/660; 435/2; 604/4.01; 604/5.01; 604/5.02; 604/5.04; 604/6.09

(58) Field of Classification Search ............ 210/321.79, 210/321.8, 321.88, 321.89, 435, 483, 488, 210/489, 490, 491, 500.23, 500.36, 500.38, 210/500.41, 503, 506, 508, 645, 650, 651, 210/660; 435/2, 4; 604/4.01, 5.01, 5.02, 604/5.04, 6.09
See application file for complete search history.

(56) References Cited

U.S. PATENT DOCUMENTS

| 5,024,767 | A | * | 6/1991 | Kubo et al. ............... 210/682 |
| 5,032,281 | A |   | 7/1991 | Nagamatusu et al. |
| 5,151,192 | A | * | 9/1992 | Matkovich et al. .......... 210/646 |
| 5,403,917 | A |   | 4/1995 | Boos et al. |
| 5,679,260 | A | * | 10/1997 | Boos et al. ................. 210/723 |
| 5,679,775 | A | * | 10/1997 | Boos et al. ................. 530/351 |
| 5,866,673 | A | * | 2/1999 | Muller et al. ............... 528/310 |
| 6,461,517 | B1 | * | 10/2002 | Miwa et al. ................. 210/690 |
| 6,478,967 | B1 | * | 11/2002 | Muller ........................ 210/650 |
| 6,849,185 | B1 | * | 2/2005 | Wu et al. .................... 210/660 |
| 6,861,001 | B2 | * | 3/2005 | Lee et al. .................... 210/651 |
| 6,913,696 | B1 | * | 7/2005 | Korngold et al. ............ 210/640 |
| 2003/0068317 | A1 | * | 4/2003 | Lee et al. ................. 424/140.1 |
| 2003/0080056 | A1 | * | 5/2003 | Boos et al. ................. 210/634 |
| 2006/0151374 | A1 | * | 7/2006 | Wu et al. ............... 210/321.77 |
| 2006/0264355 | A1 | * | 11/2006 | Storr et al. ..................... 514/2 |

FOREIGN PATENT DOCUMENTS

| DE | 39 26 539 A1 | 2/1991 |
| DE | 690 10 124 | 10/1994 |
| DE | 44 35 612 A1 | 4/1996 |
| DE | 195 15 554 A1 | 10/1996 |
| DE | 197 40 770 A1 | 3/1999 |
| DE | 199 38 394 A1 | 2/2000 |
| DE | 199 63 420 A1 | 7/2001 |
| EP | 1 002 566 A2 | 5/2000 |
| EP | 1 316 355 A2 | 6/2003 |

OTHER PUBLICATIONS

Ginsburg, et al., "Can we learn from the pathogenetic strategies of group A hemolytic streptococci how tissues are injured and organs fail in post-infectious and inflammatory sequealae" FEMS Immunology and Medical Microbiology 25 (1999) 325-338 - 1999.

* cited by examiner

*Primary Examiner*—John Kim
(74) *Attorney, Agent, or Firm*—Fulbright & Jaworski L.L.

(57) ABSTRACT

A device for removing bacterial lipopolysaccharides and lipoteichoic acids from blood or plasma in an extracorporeal perfusion system contains, in a housing that can be incorporated into the perfusion system, a hollow fiber material that is suitable for the selective removal of bacterial lipopolysaccharides and lipoteichoic acids, the device being arranged in such a way that the blood or plasma entering through a first opening of the housing must pass through the hollow fiber material before it leaves through a second opening of the housing and is directed to the rest of the perfusion circuit.

27 Claims, No Drawings

DEVICE FOR REMOVING BACTERIAL LIPOPOLYSACCHARIDES AND/OR LIPOTEICHOIC ACIDS FROM PROTEIN-CONTAINING FLUIDS AND ITS USE FOR THE TREATMENT OF SEPSIS

German Patent application 102 58 944.5 filed Dec. 17, 2002 is incorporated herein by reference.

The present invention relates to a device for removing lipopolysaccharides (LPS, endotoxins) and/or lipoteichoic acids (LTA) from protein-containing fluids, especially from blood or plasma, and the use of the said device for the treatment of patients with diseases that are caused by the invasion of gram-negative and/or gram-positive bacteria.

When there is bacteremia in the human bloodstream, serious, so-called septic complications or disease courses can often develop.

In 50 to 95% of patients with severe sepsis or septic shock, a lethal outcome is to be expected despite all therapeutic measures (Stone, R., Science (1994) 264: 365-367). There has been a significant increase in the incidence of sepsis in recent years. The reasons for this include the increasing diagnostic and therapeutic use of catheters, endoscopes, implants of prostheses, major surgery, the use of immunosuppressants, the increased number of elderly patients and bacteria's increasing resistance to antibiotics. Infections of patients in intensive care are nowadays caused primarily by resistant bacteria (Vincent, I. L., JAMA (1995) 274: 639-644).

The endotoxins (lipopolysaccharides, LPS) released during and after bacteriolysis and drug-induced antibiosis are mainly responsible for the pathogenicity of the gram-negative bacteria.

Lipopolysaccharides, as constituents of the outer membrane of gram-negative bacteria, are made up of three structurally different regions. The carrier of the toxic properties is lipid A. This subregion with a molecular weight of 2000 dalton consists of a phosphorylated D-glucosamine disaccharide, to which several long-chain fatty acids are bound in the form of esters and amides (Bacterial Endotoxic Lipopolysaccharides, Morrison, D. C., Ryan, J. L. eds., 1992, CRC Press). The bacterial lipopolysaccharides (LPS) are the initiating mediators and principal toxins in the pathogenesis of septic shock. The clinical picture of sepsis often correlates with the level of the LPS concentration in the patients' blood (Nitsche, D. et al., Intensive Care Med., 12 Suppl., 1986, 185 ff). The lipopolysaccharides stimulate the body's phagocytes, called macrophages, to produce and release inflammatory mediators such as TNF $\alpha$ and interleukins.

Removal of LPS in particular, but also of the endogenous inflammatory mediator TNF $\alpha$, has therefore been the approach for treating sepsis patients up till now.

It has been established, however, that not only the LPS of the gram-negative bacteria play a large part, but also that infections by gram-positive bacteria, which do not contain any LPS, lead to septic complications, and in particular the dangerous hospital germs such as *Staphylococcus aureus* have proved particularly pernicious.

Almost 50% of sepsis patients have an infection with gram-positive bacteria. About 30% of the patients have a mixed bacterial infection.

The toxins of the gram-positive bacteria, the lipoteichoic acids (LTA), are also located in the cell wall and are released during lysis of the bacteria. The LTA consist of glycerol or ribitol polymers, which are linked to glycolipids or phosphatidyl glycolipids via 1→3 phosphodiester bonds. The polyglycerol or ribitol chains additionally carry glucose and/or N-acetylglucosamine residues. The LTA stimulate, similarly to the LPS, monocytes and other immunocompetent cells to produce cytokines (Mattson, T., FEMS Immunol. Med. Microbiol. (1993) 7: 281-288). The deleterious biological mediator cascade is mediated or triggered, as with LPS, via soluble and membrane-bound receptors that are present in the bloodstream (Cleveland M. G., Infect. Immun. (1996) 64: 1906-1912).

LTA flowing into the bloodstream binds to the cells of the monocyte-macrophage system and stimulates the latter to increased production and release of mediators (cytokines). As the initial mediator and potent pro-inflammatory stimulus, first the tumor necrosis factor $\alpha$ is synthesized and secreted into the bloodstream. The biologically active form of TNF $\alpha$ consists of an aggregate of three identical polypeptide chains (157 amino acids, molecular weight: $17.4 \times 10^3$ dalton; Ziegler, E. J., N. Engl. J. Med. 318 (1999) 1533 ff). The subsequent biological signal amplification via interleukins, leukotrienes, prostaglandins and interferons (mediator cascade) can finally cause severe disturbances of homeostasis of various biological control systems and organ systems, for example the clinical picture of septic shock.

Accordingly, the lipopolysaccharides (LPS) as initiating toxins of gram-negative bacteria and the lipoteichoic acids (LTA) as highly potent pyrogens of gram-positive bacteria, play a key role in the pathogenesis of sepsis.

Alongside removal of the septic focus by surgery and the administration of antibiotics, new therapeutic approaches that go beyond sanitation of the source of sepsis, such as plasmapheresis, and the administration of immunoglobulins and antibodies against LPS (Bone, R. C., Crit. Care Med. (1995) 23: 994-1000) or TNF $\alpha$ (Fisher, C. J., N. Engl. J. Med. (1996) 334: 1697-1702) have not provided a substantial improvement in the prognosis for a sepsis patient.

Plasmapheresis (plasma replacement treatment) is an unselective and inefficient technique. As well as eliminating toxins and pro-inflammatory cytokines, protective, anti-inflammatory mediators are also removed from the patient. A single cycle of therapy requires a replacement volume of approx. 12 liters of plasma. Accordingly, about 50 donors are needed, and this involves an increased risk with respect to additional infections and allergic reactions.

Antibody therapy methods also have serious deficiencies and disadvantages. The costs of the technically expensive extraction, purification and characterization of the relevant antibodies are very high and there is the risk of allergic reaction (neutralizing immune response) of the body to the antibodies. With regard to LPS antibodies, the high rates of failure of therapy can be attributed among other things to the excessively low specificity and affinity between the very heterogeneous LPS molecules and the monoclonal and polyclonal antibodies used. In this connection, multicenter clinical studies had to be terminated early (Luce, J. M., Crit. Care Med. 21 (1993), 1233 ff).

Another procedure for the neutralization or elimination of pathogenic blood components consists of treating whole blood or plasma in an extracorporeal perfusion system using appropriate adsorbent materials.

The following adsorbent materials have been disclosed as potentially suitable for extracorporeal elimination of lipopolysaccharides from whole blood and/or plasma:

Porous carrier materials with immobilized polymyxin B are described in U.S. Pat. No. 4,576,928; DE 39 32 971. However, the clinical application of these affinity carriers is very problematic, because the ligand polymyxin B causes severe nephro- and neurotoxic damage on its release into the bloodstream.

The polyethylene-imine-modified bead celluloses disclosed in DE 41 13 602 A1 have very low binding capacity for LPS. If they are used in an extracorporeal perfusion system, therefore, the medically tolerable extracorporeal dead volume would be exceeded.

The H.E.L.P method described for the elimination of LPS and TNF α (DE 44 35 612 A1) is complex and therefore imposes high requirements on its operation in an intensive care unit. The system requires a very large extracorporeal dead volume and therefore, for hemodynamic reasons, is less advantageous for the patient being treated. Another disadvantage of this plasma perfusion technique is that in addition to LPS and TNF α, fibrinogen—which is essential for plasma coagulation—is also eliminated very effectively. Therefore, depending on the starting concentration of fibrinogen, use of the H.E.L.P. method is limited to a maximum of 2-3 consecutive treatments, which is in many cases insufficient for effective treatment of the patient.

Compared with the anion exchanger material described in Example 2 of DE 195 15 554 A1, the hollow fiber-based anion exchanger materials presented in the present invention have the advantage that they cannot release any glucans. The latter disturb the analytical detection of bacterial endotoxins in the patient's plasma. Furthermore, glucans can cause unwanted hemolysis and unwanted immune stimulation in the patient.

The present invention was based on the problem of providing a possible treatment and a suitable device therefor, with which the disadvantages of the methods employed to date can be avoided, and which permit effective treatment of sepsis patients in general, regardless of the type of causative bacteria.

This problem is solved according to the invention with a device for removing bacterial endotoxins and lipoteichoic acids from blood or plasma in an extracorporeal perfusion system, comprising a hollow fiber material suitable for selective removal of bacterial endotoxins and lipoteichoic acids, in a housing that can be incorporated in the perfusion system. The device according to the invention is arranged so that blood or plasma entering through a first opening in the housing must pass through the hollow fiber material before it leaves the housing through a second opening and rejoins the perfusion circuit.

For such a device to be used for adsorption apheresis, among other things the following conditions must be met:
1. Elimination of pathogens should be as selective and efficient as possible.
2. The binding capacity of the adsorbents used should satisfy optimum practical requirements.
3. It must be possible to sterilize the adsorbents with heat or gamma radiation, without loss or alteration of their properties.
4. The adsorbents should permit a sufficiently high flow rate of up to 200 ml/min.
5. The method of elimination must display the medically necessary biocompatibility and hemocompatibility and must not impair any physiological control systems and protective mechanisms, for example the immune, complement or coagulation system.

A person skilled in the art will be able to find suitable hollow fiber adsorbent materials according to this profile of requirements. In principle, hollow fiber materials can be used that are made from polyamide, polysulfone, polyether, polyethylene, polypropylene, polyester or derivatives and/or mixtures of these polymers. In an especially preferred embodiment of the invention the hollow fibers consist of nylon.

Suitable hollow fiber materials according to the invention are based on affinity membranes, as described for example in U.S. Pat. Nos. 5,053,133, 5,766,908, and in WO96/22316. These membrane base materials can be modified by known methods and in particular by graft polymerization, in this connection see for example WO96/22316, in which an appropriate method is described. Other derivatization methods for appropriate polymer materials, suitable for the production of hollow fiber adsorbent materials, are also known to a person skilled in the art and can be used within the scope of the present invention.

The hollow fiber materials according to the invention are preferably arranged in the device according to the invention in such a way that there is effective flow of blood or plasma through them, ensuring maximum wetting of the hollow fiber membrane so that optimum adsorption of the LPS and LTA onto the hollow fiber adsorbent materials can take place. Preferred arrangements of the hollow fiber materials in a device according to the invention are disclosed in WO98/57733, WO98/33581, WO98/19777 or WO98/28064, and an especially preferred arrangement is moreover described in EP 1 002 566.

As well as the hollow fiber materials, a device according to the invention can have additional materials, e.g. flat membranes, between the hollow fibers, which can often give a further increase in adsorption and separation performance. Corresponding adsorber arrangements are described in EP 0 956 147.

Both the materials disclosed in the aforesaid documents and the methods of modification and ultimate arrangements in adsorbers can be employed in the device according to the invention. Other arrangements, materials and methods of modification are, however, also included in the present invention, provided they permit effective removal of LPS and LTA from blood and plasma, and otherwise satisfy the aforesaid requirements 1 to 5 for adsorption apheresis.

To make the removal of LPS and LTA from blood or plasma particularly efficient, the device employs hollow fibers that are modified chemically in such a way that the charged LPS and LTA molecules are bound particularly well to the hollow fiber material and are therefore removed from the blood or plasma. Preferably, chemical modification of the hollow fiber material is carried out, and graft polymerization (see above) has proved especially favorable for the said modification, compounds being grafted onto the hollow fiber material that display good binding capacity for LPS and/or LTA. Grafting-on of anion exchanger groups has also proved especially advantageous. These anion exchanger groups are especially advantageous when in the form of longer chains with a large number of cationic groups, called tentacles. These tentacle-like extensions on the base material are able to bind several LPS or LTA molecules, producing a further increase in efficiency of the hollow fiber material. This modification of the hollow fiber material by means of tentacles preferably employs synthetic and/or semisynthetic and/or natural polycationic chains, and the said chains can be in linear or branched form. Modification of the hollow fiber materials according to the invention with cationic or polycationic chains that have tertiary and/or quaternary amines is especially preferred.

Preferred anion exchanger groups on the hollow fiber materials include di- or trialkylaminoalkyl, di- or trialkylaminoaryl-, di- or triarylaminoalkyl, di- or triarylaminoaryl, di- or trialkylammoniumalkyl- di- or triarylammoniumalkyl, di- or triarylammoniumaryl- and di- or trialkylammoniumaryl residues. Furthermore, polymers from amino acids that are positively charged or contain tertiary or quaternary amino groups, such as polylysine, polyarginine or polyhistidine or copolymers or derivatives thereof are suitable as anion exchanger materials within the scope of the invention, as well as polyethylene-imine.

In quite especially preferred embodiments of the invention, the device contains a polyamide hollow fiber material modified with diethylaminoalkyl or diethylaminoaryl residues, in particular diethylaminoethyl polyamide.

Furthermore, it is preferred to arrange the device in such a way that it can be used as a replaceable filter cartridge for an existing perfusion system. This can be inserted easily into the perfusion system and can have a small volume, on account of the high binding capacity and specificity of the hollow fiber material used, so that a greatly reduced dead volume can be achieved in comparison with systems described hitherto. Surprisingly, a device according to the invention can be made as a cartridge with dimensions of for example 12 cm long and 5 cm in diameter, which can be used extremely effectively in an extracorporeal perfusion system. The cartridge in this example has a dead volume of only approx. 115 ml. Therefore it is especially preferred, within the scope of the present invention, to dimension the cartridges so that the dead volume is <150 ml and preferably 80 to 130 ml.

As it could be shown that the said filter cartridges can remove LPS and LTA effectively and selectively, merely this small dead volume provides surprising and considerable advantages relative to the state of the art in addition to the possibility newly discovered according to the invention, of removing LPS and LTA simultaneously in one implementation. After the end of treatment and cleaning of the apparatus or even for carrying out an extended (continuous) blood or plasma perfusion, a new cartridge can simply be inserted.

Within the scope of the present invention, it was found that the relevant hollow fiber materials eliminate both LPS and LTA at physiological pH by adsorption from whole blood and/or blood plasma, at high selectivity and capacity.

It was found that even at physiological pH, only a small, compositionally safe amount of blood and plasma proteins are adsorbed. Fibrinogen, in particular, is only removed from the patient's blood to a quite small extent (<2%) within the scope of the present invention, so that there is hardly any impairment of the natural coagulation cascade when using the device according to the invention. Owing to the extraordinarily high binding capacity for LPS on the one hand and LTA on the other hand, the device according to the invention makes it possible, for the first time, to treat sepsis regardless of whether the disease is caused by gram-positive or gram-negative bacteria, or even if there is a mixed bacterial infection.

A further object of the invention is accordingly the use of the hollow fiber materials described, and contained in the device according to the invention, for making a means for eliminating lipopolysaccharides and/or lipoteichoic acids from body fluids, in particular from blood or plasma.

The hollow fiber materials used according to the invention, which are preferably selected from the group comprising polyamides, polysulfones, polyethers, polyethylene, polypropylene or polyesters and derivatives and/or mixtures of these materials, permit effective elimination of LPS and/or LTA from a patient's blood circulation and can therefore be used advantageously in an adsorption apheresis apparatus. As a rule, in such apparatus there will firstly be separation of whole blood into plasma and corpuscular blood components, then the plasma is directed over the adsorbent material and after that the corpuscular blood components are returned to it.

The hollow fiber materials used as adsorbents according to the invention are, in a preferred embodiment, modified chemically in such a way that optimum LPS or LTA adsorption can take place thereon. Modification of the hollow fibers by graft polymerization is especially preferred, and the grafting-on of anion exchanger groups, especially in the form of so-called tentacles, i.e. chain-like, branched molecules with as many anion exchanger groups as possible, is preferred.

An especially preferred hollow fiber material is a DEAE-modified polyamide.

As already mentioned above, with respect to the device according to the invention, it is advantageous to arrange the means in the form of a filter, if possible in the form of a disposable cartridge, ensuring easy and safe use.

The means produced according to the invention can be used especially advantageously for the treatment of patients with sepsis and especially with septic shock, since they remove the bacterial pyrogens from the patient's blood owing to the good selectivity and specificity for LPS and LTA, without further stimulation of the inflammatory mediator cascade. Because of the high specificity for LPS and for LTA, it becomes possible to treat patients with the same apparatus and the same means, regardless of whether they are suffering from sepsis caused by gram-positive or gram-negative bacteria or by both types.

The corresponding use of the device according to the invention or of the means produced according to the invention for removing LPS and/or LTA from body fluids, especially blood or plasma, and especially for the treatment of patients with sepsis even as far as septic shock, is therefore a further object of the present invention. Especially advantageously, the device according to the invention or the means produced according to the invention are used in an extracorporeal perfusion system, which provides particularly effective removal of bacterial pyrogens from the patient's blood and leads to exceptionally successful treatment of patients. During application according to the invention, moreover, LPS and/or LTA are removed very selectively, whereas endogenous proteins are only removed to a very small extent, if at all, or said removal only applies to proteins that are easily replaceable and whose removal is not notably stressful for the already much debilitated sepsis patient.

Within the scope of the present invention it is also possible to use the adsorbent materials described above for the isolation and enrichment of LPS and LTA, therefore the said use of the device according to the invention is a further object of the present invention. The said isolation and enrichment can take place from any fluids, preferably from blood or plasma, and this can be done for any purposes, though in particular for analysis and/or diagnosis.

The invention is explained in more detail in the following examples.

EXAMPLE 1

Adsorption and Elimination of LPS from Human Plasma on Perfusion through the Adsorber Module According to the Invention The adsorber module used (length 12 cm, diameter 5 cm) was packed with hollow polyamide fibers according to EP 1 002 566 A2. The surface of the hollow fibers was modified according to the invention, with tentacles that were grafted on by polymerization and functionalized with DEAE groups. The module was first washed and conditioned with 500 ml of Ringer's solution (140 mmol/l NaCl; 2 mmol/l $CaCl_2$ and 4 mmol/l KCl), prior to perfusion with human plasma.

140 ng (corresponding to approx. 1400 endotoxin units, EU) of radioactive $^3$H-LPS (*E. coli* K12 strain LCD 25) with a specific activity of $4 \times 10^5$ dpm/µg was added to 100 ml of human plasma. This mixture was pumped through the hollow fiber module according to the invention at room temperature using a peristaltic pump at a flow rate of 20 ml/min, and eluate fractions (5 ml) were obtained every 15 seconds. Subsequent liquid scintillation measurement of radioactivity showed that $^3$H-labeled LPS could not be detected in any of the fractions obtained.

Quantitative determination of LPS in the perfusate was carried out in parallel using the chromogenic kinetic Limulus-Amoebocyte-Lysate test (supplier: BioWhittaker). This trace-analysis measurement technique also showed that the LPS added to the human plasma was no longer detectable in the perfusate and therefore had been eliminated completely.

EXAMPLE 2

Adsorption and Elimination of LTA from Human Plasma on Perfusion through the Adsorber Module According to the Invention The adsorber module used (length 12 cm, diameter 5 cm) was packed with hollow polyamide fibers according to EP 1 002 566 A2. The surface of the hollow fibers was modified according to the invention, with tentacles that were grafted on by polymerization and functionalized with DEAE groups. The module was first washed and conditioned with 500 ml of Ringer's solution (140 mmol/l NaCl; 2 mmol/l CaCl$_2$ and 4 mmol/l KCl), prior to perfusion with human plasma.

200 μg LTA from *Streptococcus pyogenes* (supplier: Sigma-Aldrich) was added to 100 ml human plasma, which was then pumped at room temperature through the adsorber module described above by a peristaltic pump at a flow rate of 20 ml/min. 5-ml eluate fractions were obtained at 15-second intervals and were investigated for LTA activity.

This was carried out using a whole-blood stimulation test. For this, an aliquot from each of the eluate fractions obtained was added in a ratio of 6:1 (v/v) to freshly obtained, heparinized whole blood from a healthy donor, which was then incubated at room temperature for 24 hours. After centrifugation, obtaining the corresponding plasma fraction, interleukin-6 (IL-6) was determined quantitatively in all the eluate fractions obtained and incubated, using an ELISA test (supplier: Biosource).

The result found was that none of the perfused plasma fractions led to LTA-mediated stimulation of IL-6 biosynthesis, i.e. to an increased IL-6 concentration relative to a control (perfused aliquot of a plasma sample without addition of LTA). Therefore, with the aid of this highly sensitive bioassay it was demonstrated, admittedly indirectly, but highly significantly, that the adsorber module used according to the invention provides complete elimination of bacterial lipoteichoic acid from human plasma.

EXAMPLE 3

Simultaneous Adsorption and Elimination of LPS and LTA from Human Plasma on Perfusion through an Adsorber Module According to the Invention The adsorber module used (length 12 cm, diameter 5 cm) was packed with hollow polyamide fibers according to EP 1 002 566 A2. The surface of the hollow fibers was modified according to the invention, with tentacles that were grafted on by polymerization and functionalized with DEAE groups. The module was first washed and conditioned with 500 ml of Ringer's solution (140 mmol/l NaCl; 2 mmol/l CaCl$_2$ and 4 mmol/l KCl), prior to perfusion with human plasma.

2000 EU of bacterial LPS (*E. coli* 055: B5 endotoxin; supplier: BioWhittaker) and 100 μg LTA (Streptococcus pyogenes; supplier: Sigma-Aldrich) were added to 100 ml of human plasma.

In accordance with the test procedure in Example 2, corresponding perfusate fractions were obtained and were investigated for any LTA or LPS activity present, using the whole-blood stimulation test described. The analysis showed that LTA or LPS activity could not be detected in any of the perfusates.

The invention claimed is:

1. A method of treating sepsis comprising treating a patient with sepsis by passing a body fluid of the patient through a device comprising a chemically modified hollow fiber material that is suitable for the collective removal of bacterial lipoteichoic acid and lipopolysacoharide such that the body fluid passes though said hollow fiber material and said hollow fiber material removes both bacterial lipoteichoic acid and lipopolysaccharide from the body fluid.

2. The method of claim 1, wherein the hollow fiber materials used are selected from the group consisting of polyamides, polysulfones, polyethers, polyethylene, polypropylene, polyesters, derivatives and mixtures thereof.

3. The method of claim 1, wherein the hollow fiber material is a polyamide.

4. The method of claim 1, wherein the hollow fiber material is modified by graft polymerization.

5. The method of claim 1, wherein tentacles, which comprise anion exchanger groups, are polymerized onto the hollow fiber material.

6. The method of claim 5, wherein the anion exchanger groups comprise at least one of a synthetic, a semisynthetic, and a natural polycationic chain, said chain being in linear or branched form.

7. The method of claim 5, wherein the anion exchanger groups comprise cationic or polycationic chains having tertiary or quaternary amines.

8. The method of claim 5, wherein the anion exchanger groups are selected from the group consisting of di- or trialkylaminoalkyl, di- or trialkylaminoaryl, di- or triarylaminoalkyl, di- or triarylaminoaryl, di- or trialkylammoniumalkyl, di- or triarylammoniumalkyl, di- or triarylammoniumaryl, di- or trialkylammoniumaryl residues, polymers from amino acids that are positively charged or contain tertiary or quaternary amino groups, and polyethylene-imine.

9. The method of claim 1, wherein the hollow fiber material comprises a polyamide modified with diethylaminoethyl groups.

10. The method of claim 1 , wherein the device is arranged in the form of a filter module.

11. The method of claim 10, wherein the filter module has a dead volume of <150 ml.

12. The method of claim 1, wherein the device permits a flow rate of up to 200 ml/minute.

13. The method of claim 1, wherein said device is designed for application in a plasma perfusion system.

14. The method of claim 1, wherein said device is suitable for the treatment of diseases caused by at least one of gram-negative or gram-positive bacteria.

15. A method of treating sepsis comprising treating a patient with sepsis by passing a body fluid of the patient through a device for removing both bacterial lipopolysaccharides lipoteichoic acids from a body fluid, said device comprising a housing that can be incorporated into the perfusion system, a chemically modified hollow fiber material that is suitable for the collective removal of both bacterial lipoteichoic acids and lipopolysaceharides in the housing, the device being arranged such that the blood or plasma entering through a first opening of the housing must pass through the hollow fiber material before it leaves through a second opening of the housing and is directed to the rest of the perfusion system, wherein said hollow fiber material comprises at least one polymer selected from the group consisting of polyamide, polysulfone, polyether, polyethylene, polypropylene, polyester, derivatives and mixtures thereof, wherein said hollow fiber material has tentacles comprising an anion exchange group polymerized thereon by graft polymerization, wherein the anion exchange group comprises at least one of the group consisting of a synthetic polycationic chain, a semisynthetic polycationic chain and a natural polycationic chain, wherein said synthetic, semisynthetic and natural polycationic chains are linear or branched and wherein said device has a dead volume <150 ml.

16. The method of claim 15, wherein the device is used in an extracorporeal perfusion system.

17. The method of claim 15, wherein the patient is afflicted with septic shock.

18. The method of claim 15, wherein the body fluid is blood or plasma.

19. The method of claim 15, wherein the device is a replaceable filter cartridge.

20. The method of claim 15, wherein the hollow fiber material comprises nylon.

21. The method as claimed in claim 15, wherein the anion exchange groups comprise a synthetic polycationic chain.

22. The method as claimed in claim 15, wherein the anion exchange groups comprise a cationic chain or a polycationic chain including at least one of a tertiary amine or a quaternary amine.

23. The method as claimed in claim 15, wherein the anion exchange groups are selected from the group consisting of di- or trialkylaminoalkyl, di- or trialkylaminoaryl, di- or triarylaminoalkyl, di- or triarylaminoaryl, di- or trialkylammoniumalkyl, di- or triarylammoniumalkyl, di- or triarylammoniumaryl or di- or trialkylammoniumaryl residues, polymers from amino acids that are positively charged or contain a tertiary or a quarternary amino group, and polyethyleneimine.

24. The method as claimed in claim 15, wherein the hollow fiber material comprises a polyamide modified with diethylaminoethyl groups.

25. The method as claimed in claim 15, wherein the hollow fiber material permits a flow rate of up to 200 ml/minute.

26. The method of claim 5, wherein the anion exchanger groups are positively charged.

27. The method of claim 26, wherein the anion exchanger groups are at least one of a tertiary amine and a quaternary amine.

* * * * *

UNITED STATES PATENT AND TRADEMARK OFFICE
CERTIFICATE OF CORRECTION

PATENT NO. : 7,608,189 B2
APPLICATION NO. : 10/860786
DATED : October 27, 2009
INVENTOR(S) : Seidel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 587 days.

Signed and Sealed this

Twelfth Day of October, 2010

David J. Kappos
*Director of the United States Patent and Trademark Office*